(12) United States Patent
Fahrig et al.

(10) Patent No.: US 8,331,531 B2
(45) Date of Patent: Dec. 11, 2012

(54) CONFIGURATIONS FOR INTEGRATED MRI-LINEAR ACCELERATORS

(75) Inventors: Rebecca Fahrig, Palo Alto, CA (US);
Norbert J. Pelc, Los Altos, CA (US);
Kim Pauly, Stanford, CA (US); Greig C. Scott, Palo Alto, CA (US); Amit Sawant, Mountain View, CA (US); Paul J. Keall, Palo Alto, CA (US); Lei Xing, Palo Alto, CA (US); Steven M. Conolly, Palo Alto, CA (US)

(73) Assignees: The Board of Trustees of the Leland Stanford Junior University, Palo Alto, CA (US); The Regents of the University of California, Berkeley, CA (US)

( * ) Notice: Subject to any disclaimer, the term of this patent is extended or adjusted under 35 U.S.C. 154(b) by 139 days.

(21) Appl. No.: 12/661,303

(22) Filed: Mar. 15, 2010

(65) Prior Publication Data
US 2010/0239066 A1 Sep. 23, 2010

Related U.S. Application Data

(60) Provisional application No. 61/210,089, filed on Mar. 13, 2009.

(51) Int. Cl.
*A61N 5/10* (2006.01)
*G01N 23/04* (2006.01)

(52) U.S. Cl. ............................................. 378/65; 378/63
(58) Field of Classification Search .................... 378/62, 378/65; 250/492.1, 492.3; 324/309; 600/411
See application file for complete search history.

(56) References Cited

U.S. PATENT DOCUMENTS

| | | | | |
|---|---|---|---|---|
| 5,583,908 | A * | 12/1996 | Antich et al. ................... | 378/65 |
| 2009/0022383 | A1 * | 1/2009 | Falco et al. .................... | 382/131 |
| 2009/0149735 | A1 * | 6/2009 | Fallone et al. ................ | 600/411 |
| 2010/0174172 | A1 * | 7/2010 | Ein-Gal ........................ | 600/411 |

* cited by examiner

*Primary Examiner* — Irakli Kiknadze
(74) *Attorney, Agent, or Firm* — Lumen Patent Firm

(57) ABSTRACT

The present invention provides a radiotherapy treatment apparatus that includes a treatment beam, a magnetic field disposed parallel collinear to the treatment beam, and a target that is disposed along the treatment beam. The treatment beam can be a charged particle beam, a proton beam, an electron beam, or a linear accelerator (Linac) beam. The magnetic field is from a magnetic resonance imager (MRI), a megavolt x-ray imager, or a kilovolt x-ray imager and is disposed to operate in coordination with operation of the treatment beam and to narrow the beam. The tumor is disposed to rotate with respect to the treatment beam and the magnetic field, or the treatment beam and the magnetic field are disposed to rotate up to 360° with respect to the target when mounted to a ring gantry. The apparatus can include a rotation angle dependent shim disposed to account for Earth's magnetic field.

12 Claims, 5 Drawing Sheets

(a)

(b)

CONFIGURATIONS FOR INTEGRATED MRI-LINEAR ACCELERATORS

CROSS-REFERENCE TO RELATED APPLICATIONS

This application claims priority from US Provisional Patent Application 61/210,089 filed Mar. 13, 2009, which is incorporated herein by reference.

FIELD OF THE INVENTION

The present invention relates to magnetic resonance imaging and radiotherapy. More particularly the invention relates to integrating a linear accelerator and a magnetic field of an MRI scanner during treatment radiotherapy treatment.

BACKGROUND

Radiation therapy of tumors in the lung and abdomen is currently limited by the inability to follow the motion of the tumor during the treatment. Magnetic resonance imaging has the potential to provide good images of the tumor, fast enough to allow imaging during therapy treatment. This would allow higher dose deposition in the tumor and spare the surrounding tissue. However, joining a Linac (therapy producing system) and an MR scanner is very challenging since the Linac uses electron acceleration to produce high-energy treatment photons, and these electrons can be affected by a magnetic field. In addition, the dose deposited in tissue can also be affected by a magnetic field.

Half of all cancer patients receive radiation therapy. (1) In recent years there have been tremendous advances in radiotherapy due to the use of image-guidance. However, the efficacy of image-guided radiation therapy (IGRT) for the treatment of thoracic and abdominal cancers remains limited due to geometric and dosimetric uncertainties caused by motion during dose delivery, where effective management of intrafraction motion is key to realizing the full potential of IGRT. Intrafraction motion management consists of two tasks: i) real-time estimation of tumor position and shape and, ii) corresponding real-time beam adaptation. Recent work in automatic detection of tumor volumes and adaptation of multi-leaf collimator systems during therapy addresses task two. However, with respect to task one, there is currently no method capable of directly visualizing a soft-tissue volume such as a prostate tumor or lung nodule during dose delivery. The most obvious choice is ultrasound, however soft tissue contrast is limited, and it cannot penetrate the ribs and air-filled lungs. Other options include projection radiography, which requires implantation of high-contrast beads in the tumor prior to treatment, or a calibrated monitor of external patient motion that correlates with internal tumor motion. Such approaches provide information of limited accuracy, reliability and reproducibility, and often increase interventional complications and imaging dose.

There is currently nothing available capable of directly visualizing a soft-tissue volume such as a prostate tumor or lung nodule during dose delivery. There are efforts in using linear accelerator-MRI to investigate ways to address the key issues, where the designs have the main magnetic field of the MRI scanner perpendicular to the radiation treatment beam. One group first mounts a low-field (0.2 T) permanent 'C' magnet and the Linac head on a rotating gantry with the RF source of the Linac in a separate room. Rotation is a significant engineering challenge. Another group has built a split-gradient 1.5 T system with the intent to rotate a linac around the MR system. The Linac will operate well at only one radial distance from the center of the magnet where the magnetic field is essentially zero. The major drawback of both geometries is that the therapy beam is at right angles to the main magnetic field B of the MR. The orthogonal geometry is sub-optimal for two reasons: first, the trajectories of electrons generated in the first few cm of tissue are affected by the presence of B, and deposit significantly higher skin dose than is desired; second, the electrons generated within the body next to air cavities are 'bent back' and again deposit undesired dose in adjacent tissue.

There are other groups attempting to integrate X-ray based radiation therapy and MR imaging, where only two are using an electron linac as an X-ray source. All of the above mentioned projects are using a perpendicular design characterized by the fact that the radiation beam is orthogonal to the magnetic field generated by the MRI system magnet. The main characteristic of a perpendicular design is that the dose distribution is going to be adversely affected by the existence of the magnetic field in the sense that there will be an extra dose deposited at the interface between air and tissue due to the return effect, which is going to affect healthy tissue. Also a perpendicular design, using a linac is more difficult to implement because one has to effectively isolate and decouple the operation of the linac and the MRI subsystems. It is clear that any transverse magnetic field to the accelerating structure will bend the electron beam due to the Lorentz force, which will result in no beam at the tungsten target.

Stereotactic body radiation therapy (SBRT) is used for early stage lung cancer. SBRT is a newly emerging radiotherapy treatment method to deliver a high dose of radiation to the target, utilizing either a single dose or a small number of fractions with a high degree of precision within the body. There are several trends in lung cancer, all leading to a sharp increase in the number of patients being treated with stereotactic body radiotherapy (SBRT). One of these is the increase in early stage lung cancer detection, and thus demand for treatment through CT screening programs.

Accordingly, there is a need to develop an apparatus that can provide real-time imaging of the position of a tumor while not interfering with the treatment beam, and a further need is an apparatus that can improve the quality of the treatment beam at the air-patient interface.

SUMMARY OF THE INVENTION

The present invention provides a radiotherapy treatment apparatus that includes a radiotherapy treatment beam, a magnetic field disposed at least parallel to the radiotherapy treatment beam, and a target that is disposed along the radiotherapy treatment beam.

In one aspect of the invention, the radiotherapy treatment beam is a charged particle beam.

In another aspect of the invention, the radiotherapy treatment beam is a proton beam.

In a further aspect, the radiotherapy treatment beam is an electron beam.

In yet another aspect, the radiotherapy treatment beam is a linear accelerator (Linac) beam.

According to one aspect of the invention, the magnetic field is disposed collinear with the radiotherapy treatment beam.

In another aspect, the magnetic field is from a magnetic resonance imager (MRI), where the MRI is disposed to operate in coordination with operation of the radiotherapy treatment beam.

In a further aspect of the invention, the magnetic field is disposed to narrow the radiotherapy treatment beam.

According to one aspect, the target is disposed to rotate with respect to the radiotherapy treatment beam and the magnetic field, or the radiotherapy treatment beam and the magnetic field are disposed to rotate with respect to the target. Here the rotation can include rotation up to 360°.

In another aspect of the invention, the target is a tumor.

In a further aspect, the radiotherapy treatment apparatus includes a rotation angle dependent shim disposed to account for Earth's magnetic field.

According to another aspect of the invention, a source for the magnetic field and a source for the treatment beam are mounted to a ring gantry, where the magnetic field source and the treatment beam source rotate about the target.

In yet another aspect of the invention, the radiotherapy treatment apparatus includes an x-ray imager, where the x-ray imager can include a megavolt treatment beam x-ray imager, or a kilovolt x-ray imager.

BRIEF DESCRIPTION OF THE FIGURES

The objectives and advantages of the present invention will be understood by reading the following detailed description in conjunction with the drawing, in which.

DETAILED DESCRIPTION OF THE INVENTION

Figure 1:
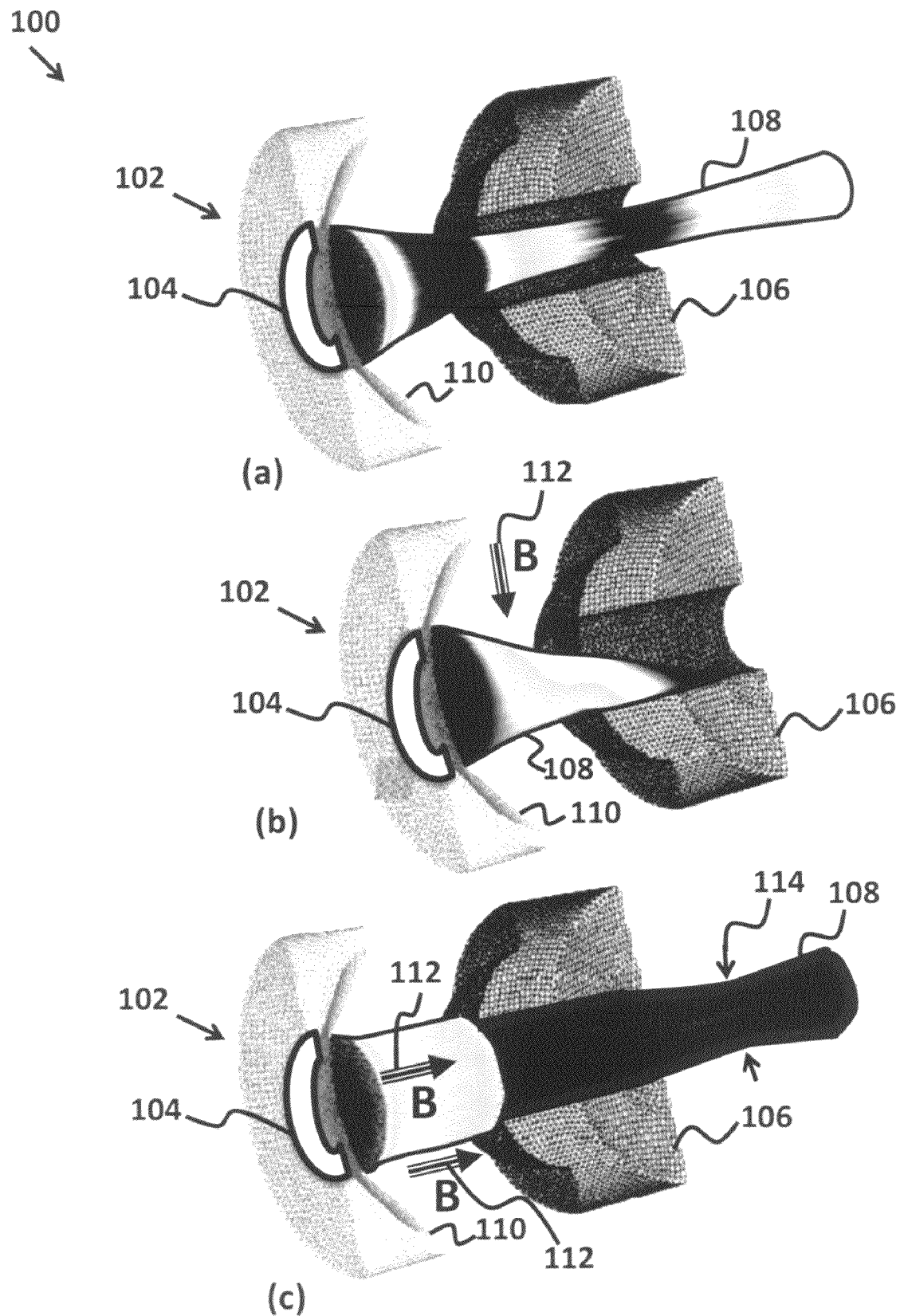
FIG. 1(a)-1(c) show a comparison of in-line versus perpendicular geometries of the Linac and MRI combination according to the present invention.

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

The current invention fundamentally changes the practice of inter- and intra-fraction motion management in radiation therapy treatment of tumors and enables more aggressive treatment strategies that employ dose escalation, tighter geometric margins and sharper dose gradients, which result in improved clinical outcomes.

Radiographic marker implantation, which is in routine use for esophagus, liver, lung, and pancreas patients is currently the most practical image guidance procedure. Gold fiducial markers are percutaneously implanted into the tumor using CT guidance. Though fiducial implantation has risk and is invasive, until robust non-invasive imaging systems are developed the markers give a high degree of confidence for image guidance procedures.

Lung tumors move with respiration up to 5 cm for free breathing. The magnitude of motion is variable and unpredictable, changing within fractions, between fractions, and between patients. Furthermore, tumor motion exhibits hysteresis, significant motion in three dimensions, in addition to variations in the baseline position of the tumor in all three dimensions and variations in the cycle-to-cycle period, shape and range of motion. All of these factors challenge the imaging, planning, and delivery of lung stereotactic body radiation therapy (SBRT).

Clinical response and motion data demonstrates both the curative potential, and potential harm of lung SBRT, and challenges the radiation oncology community to develop better targeted radiation delivery systems such as the MRI-linac according to the current invention.

Continuing advancements in imaging hardware and software such as faster gradients, dedicated coils as well as the development of sophisticated, rapid-imaging pulse sequences, led to several groups reporting on lung MRI for cancer imaging. More recently, through the use of fast acquisition techniques, real-time or near-real-time 2D and 3D imaging of the lungs has been performed to characterize lung tumor motion. Furthermore, it has been demonstrated that with strategies such as parallel imaging, even faster measurements, including non-gated, free breathing MRI, can be performed.

In this context, one aspect of the present invention (radiotherapy guidance), the fact that normal lung parenchyma presents poor signal can be an advantage. Lung tumors, which exhibit relatively higher water content and therefore higher proton density than normal lung tissue, present as high contrast objects in MR images.

The current invention is for SBRT for early stage lung cancer. SBRT is a newly emerging radiotherapy treatment method to deliver a high dose of radiation to the target, utilizing either a single dose or a small number of fractions with a high degree of precision within the body. There are several trends in lung cancer, all leading to a sharp increase in the number of patients being treated with SBRT. One of these is the increase in early stage lung cancer detection, and thus demand for treatment through CT screening programs.

The current invention enables selective radiation targeting and/or functional avoidance for key processes in tumor and normal tissues, respectively. The radiation therapy image guidance according to the invention provides real-time volumetric information of the tumor and surrounding normal tissue during the treatment itself. This information enables continuous alignment of the therapeutic radiation beam with the tumor to facilitate local control whilst synchronously avoiding overdosing critical structures using the narrowed treatment beam. The current invention uses magnetic resonance imaging (MRI) to allow near real-time volumetric imaging, and provide exquisite soft tissue contrast to identify cancerous and healthy tissues. Such a guidance apparatus not only improves current radiotherapy but also improves the ability to simultaneously visualize targets to irradiate and structures to avoid, thus providing new treatment opportunities for radiation therapy, such as non-invasively treating atrial fibrillation by creating lesions in the pulmonary vein.

The invention is an integrated MRI-linear accelerator (Linac), where the main magnetic field B is aligned, parallel or collinear, with the treatment beam that effects increased tumor control and reduced toxicity to the patient, where the magnetic field is disposed to narrow the radiotherapy treatment beam. FIGS. 1(a)-1(c) show a comparison of in-line versus perpendicular geometries of the Linac and MRI combination 100. FIG. 1(a) shows an electron gun head 102 without an influence of a magnetic field. The electron gun head 102 includes an cathode 104 and a anode 106 disposed to generate the treatment beam 108, where the cathode 104 is formed to provide a focus electrode 110. In this configuration, the absence of the magnet field precludes the use of real-time imaging from an MRI. FIG. 1(b) shows the electron gun head 102 providing the treatment beam 108 with a magnetic field (B) 112 disposed in a perpendicular direction relative to the treatment beam 108. As shown, the magnetic field (B) 112 distorts electron flow direction in the treatment beam 108. FIG. 1(c) shows the electron gun head 102 providing the treatment beam 108 with a magnetic field (B) 112 disposed collinear or parallel to the treatment beam 108. The presence of the magnetic field (B) 112 disposed collinear or parallel to the treatment beam 108 alleviates distortion to the treatment beam 108 and further provides a narrowing of the beam 114, which is desirable for isolating the exposure to the tumor and not to healthy tissue.

The current invention includes at least three system geometries that allow the two systems to function in close proximity, where the full potential of MR guidance during radiation therapy can be exploited. This invention significantly improves the patient outcomes. In addition, the invention provides excellent guidance during proton therapy, an emerging disruptive technology that provides the possibility of more highly confined dose deposition if 3D image guidance during the treatment.

Figure 2:
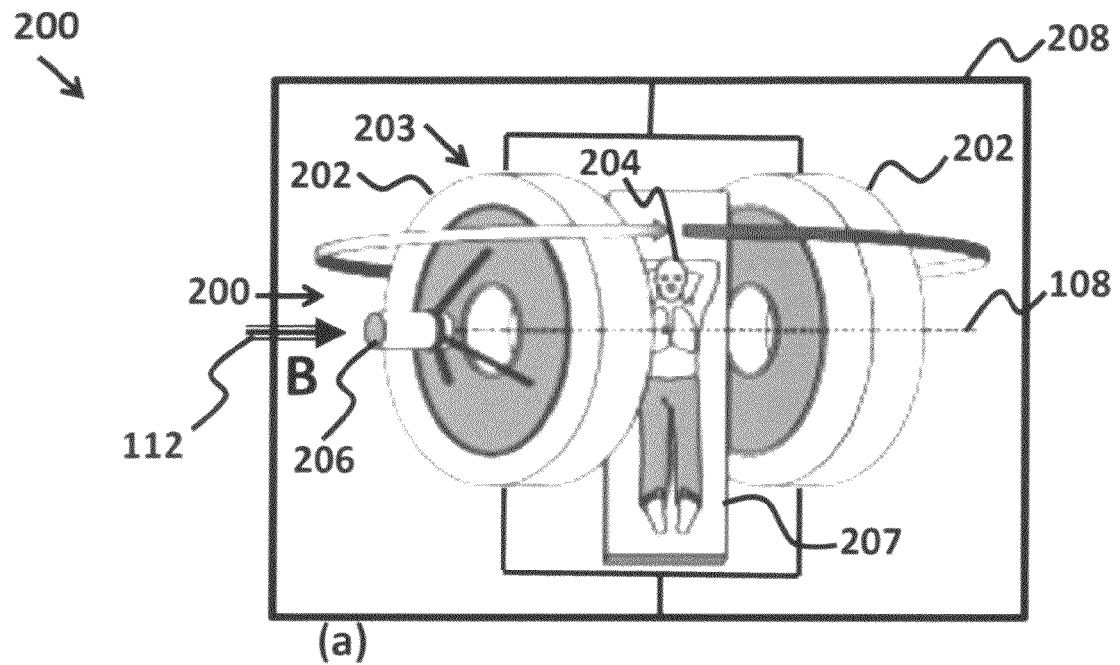
FIGS. 2(a)-2(b) show two embodiments of the Linac-MRI treatment apparatus according to the current invention.
Figure 2:
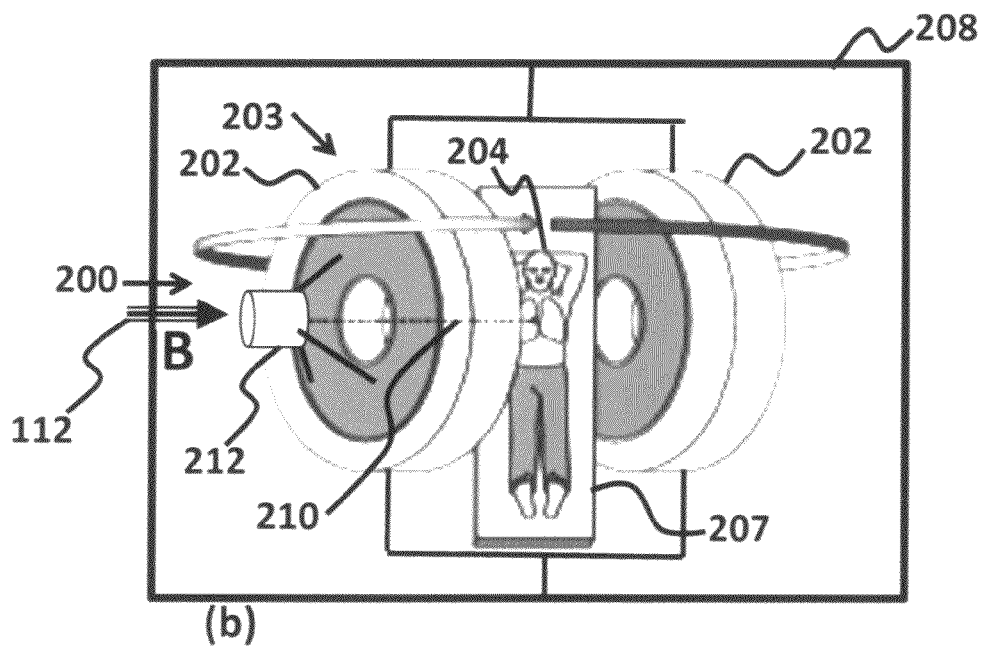

FIGS. 2(a)-2(b) show two embodiments of the Linac-MRI treatment apparatus according to the current invention, where the magnets are superconducting.

FIG. 2(a) shows the Linac beam 108 from the Linac beam generator 206 aligns with the $B_0$ field 114 of the magnets 202 with the patient 204 on a stationary bed 207 between the poles of the magnet 202, where the Linac beam generator 206 and the MRI 203 are mounted to a rotatable gantry 208 to enable rotation of the Linac beam generator 206 and the MRI 203 about the patient 204.

FIG. 2(b) shows a particle beam 210 from a compact particle accelerator 212, for example a compact proton accelerator, aligned with the $B_0$ field 114 of the magnets 202 with the patient 204 on a stationary bed 207 between the poles of the magnets 202, where the compact particle accelerator 212 and the MRI 203 are mounted to a rotatable gantry 208 to enable rotation of the compact particle accelerator 212 and the MRI 203 about the patient 204.

For the above embodiments, a sufficient gap between the magnets allows the patient 204 to be rotated with respect to the beams (108/210), providing the possibility of treatments over the full 360°. The real-time image guidance provided by the MR system 203 permits correction for any uncertainty in tumor location that arise due to 'uncontrolled' patient 204 motion. In addition, stability of both systems is maximized, as is ease of construction and room design, since the Linac high-energy beam (108/210) is always pointed in the same direction, and the relative locations of each system are constant.

In various embodiments, the invention provides the rotation of the patient and/or the MRI scanner and/or the linear accelerator-particle beam source to allow multiple, and potentially non-coplanar beam directions, including arc therapy. Proton and ion therapy beams, instead of photon beams, are within the scope of the current invention.

The geometries according to the invention lead to improved dose distribution while providing sufficient image quality for real-time tracking of moving lesions and thus improved dose delivery.

The inline design approach has the merit that is synergistically coupling the linac and the MRI system such that they can function without the need of hybrid implementations based on RF and magnetic shielding. The inline approach will focus the electrons in the electron gun and accelerating structure making the beam narrower and having a more efficient output. The penumbra is narrow for an inline magnetic field. The inline design is preferred over the perpendicular approach because of deterministic dose distribution and because one could also use treatment beams with charged particles. The present embodiment is specifically referring to electron linacs. However, the invention is generalized to proton therapy. Particle beams in particular will not be amenable to perpendicular fields, as the field will spread the particle beam based on the energy variation within each pulse across the patient surface. This effect will worsen as magnetic fields increase.

In another aspect of the invention, a pair of pulsed electromagnets are used that can be ramped up to high field (~0.2 T) during imaging and then ramped down during therapy. This technology is known as Pre-polarized MRI or pMRI. Dose deposition using this system would be equivalent to the dose in the absence of the magnetic field. According to this aspect, the pMRI can be parallel the linac beam line.

According to the invention, the pMRI apparatus can be provided with the following parameters: 70-cm gap between the magnet poles, 200 kW power, 0.20 T polarizing field, ramp up/down in 100 ms, providing 2.5 mm isotropic voxel resolution in a slice image acquired in 200 ms. Linear programming techniques are used to define the optimum design configuration for a magnet and design of minimum-power resistive shim coils. These coils are provided to produce any order shim field over an arbitrarily shaped target region, which can be placed anywhere within the coil.

In a further configuration, the invention uses a pair of pulsed electromagnets, which may be ramped up to high field (~0.2 T) during imaging and then ramped down during therapy using an electromagnet without pre-polarization. Dose deposition using this system can be equivalent to the dose in the absence of the magnetic field. Concurrent MR imaging and therapy would not be possible, however using position estimation models based on the prior MR data and concurrent additional, e.g. optical imaging, an accurate estimation of the temporally changing anatomy could be made during therapy, with MR images acquired at a frequency that optimized total treatment time and accuracy.

Figure 3:
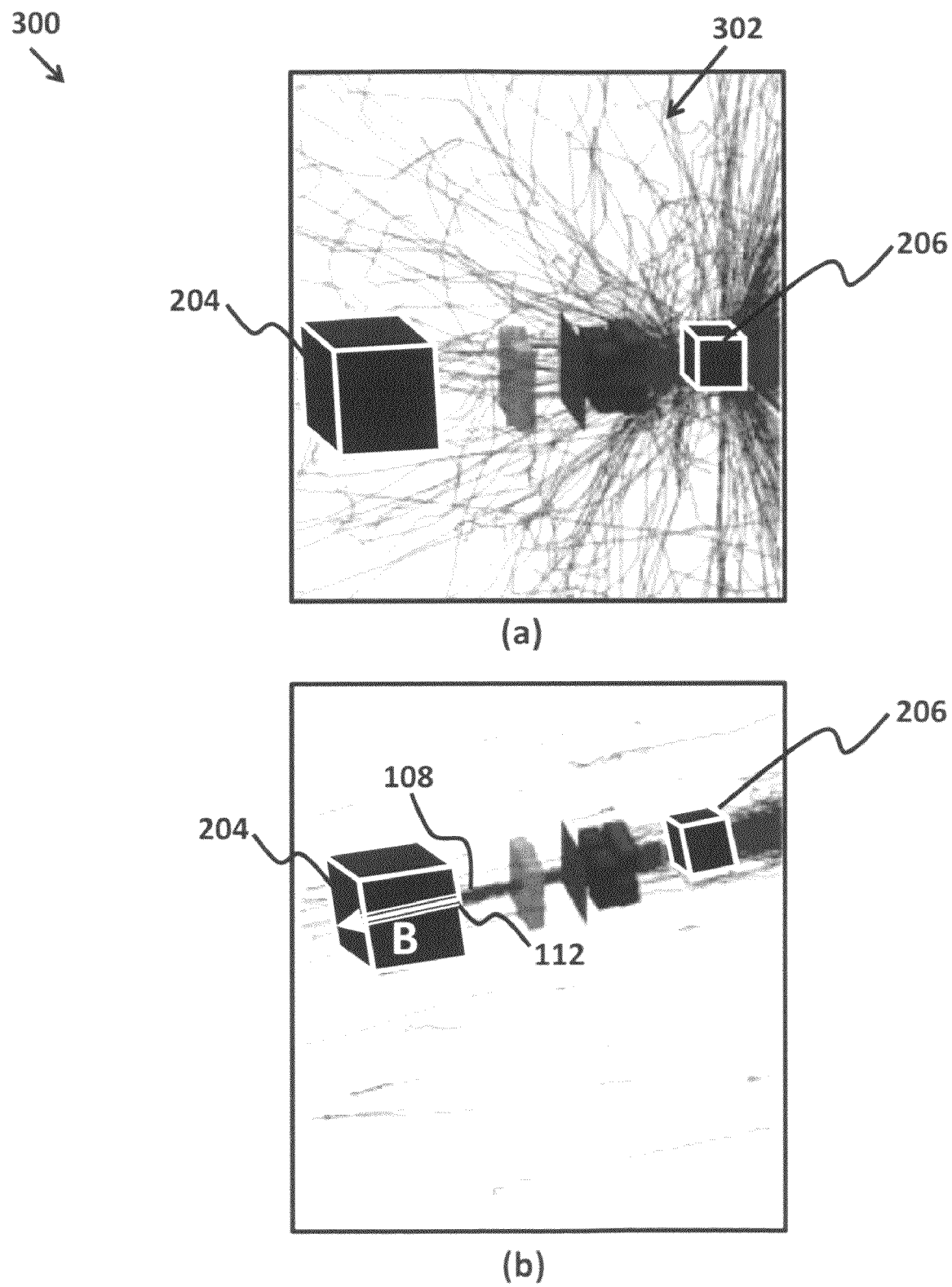
FIGS. 3(a)-3(b) show results of a finite element program used to simulate electron trajectories in an x-ray tube when placed in a magnetic field according to the current invention.

FIGS. 3(a)-3(b) shows results of a finite element program 300 (OPERA-3d; Vector Fields, UK) that was used to simulate electron trajectories in an x-ray tube when placed in a magnetic field. Thermionic emission was modeled and the electrostatic Poisson's equation was solved numerically to obtain the electrostatic field, including the effects caused by space charge in the electron beam. The model was verified by the inventors using a pin-hole experiment. In these figures, the Linac head 302 is on the right, 'patient' 204 is shown. Presence of the uniform magnetic field directs scattered electrons to the patient 204, leading to an undesirable skin dose. Deflection coils are provided to reduce this effect.

As shown in FIG. 3(a), trajectories are seen of charged particles 302 created in Linac collimators by a 6 MV therapy beam without an external field, which represent scattered electrons from Linac 206 that would normally be emitted in all directions am may deposit unwanted skin dose. Shown in FIG. 3(b), electromagnets having a magnetic field 112 are placed close to the head (see FIG. 2) of the Linac 206 to remove these electrons 302 and confine them in a beam 108 to spiral around with the field lines of the magnetic field 112, where a uniform 0.5 T field is applied in the direction of the therapy beam 108.

Figure 4:
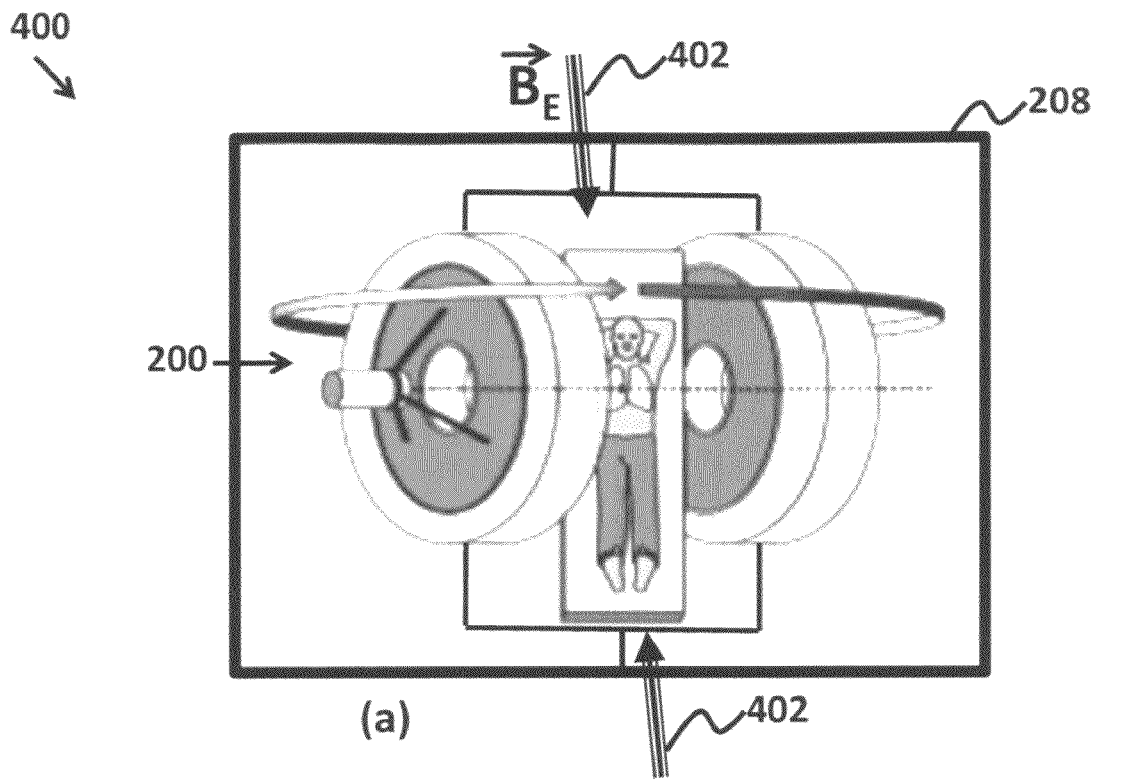
FIGS. 4(a)-4(b) show the use of a rotation angle dependent shim to account for the presence of Earth's magnetic field according to the current invention.
Figure 4:
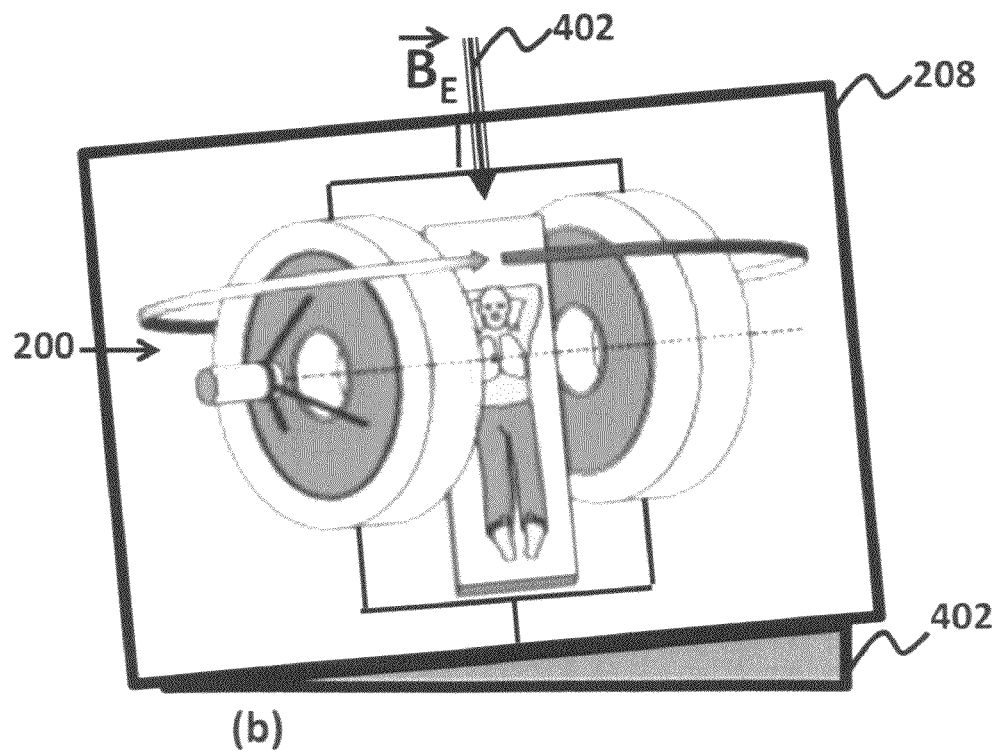

Rotating the MRI system is challenged by the change in orientation of the system with respect to Earth's magnetic field and also by high structural integrity requirements of the MRI system to achieve ppm field uniformity. As shown in FIG. 2(a) the non-rotating system is not subject to a dynamic influence of Earth's magnetic field. FIGS. 4(a)-4(b) show the invention adjusted to account for the presence of Earth's magnetic field 400 according to the current invention. FIG. 4(a) shows the rotating Linac-MRI treatment apparatus 200 of FIGS. 2(b)-2(c) with the presence of Earths magnetic field $B_E$ 402. According to the current invention, FIG. 4(b) shows a rotation angle dependent shim 404 disposed to account for the changing orientation with respect to the Earth's magnetic field, where the mounting system includes the strong ring gantry 208 to account for the mechanical requirements.

Figure 5:
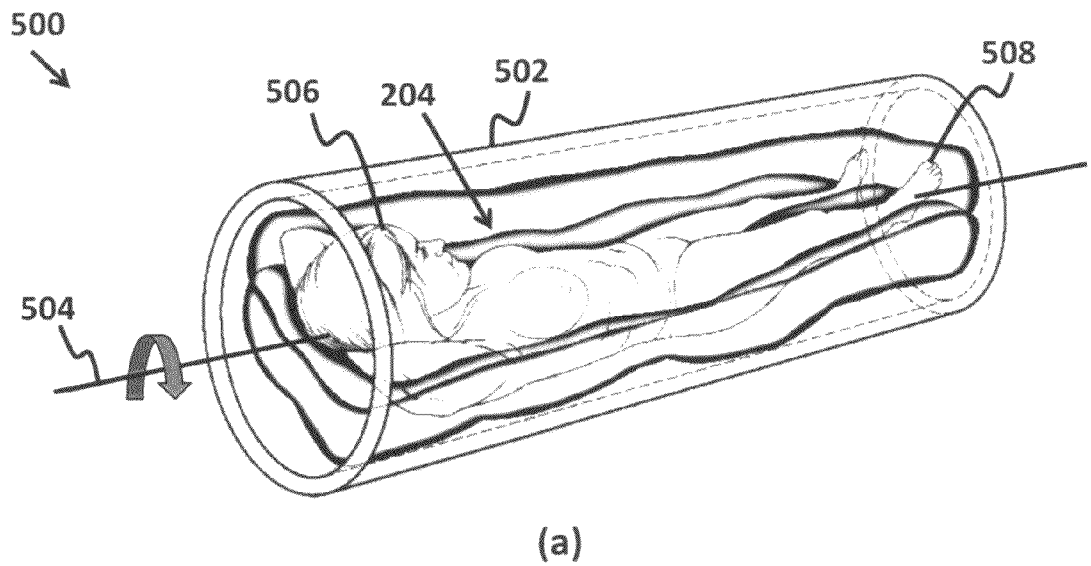
FIGS. 5(a)-5(b) show a stationary treatment beam source along the magnetic field with a patient rotating about an axis of a supine position according to the current invention.
Figure 5:
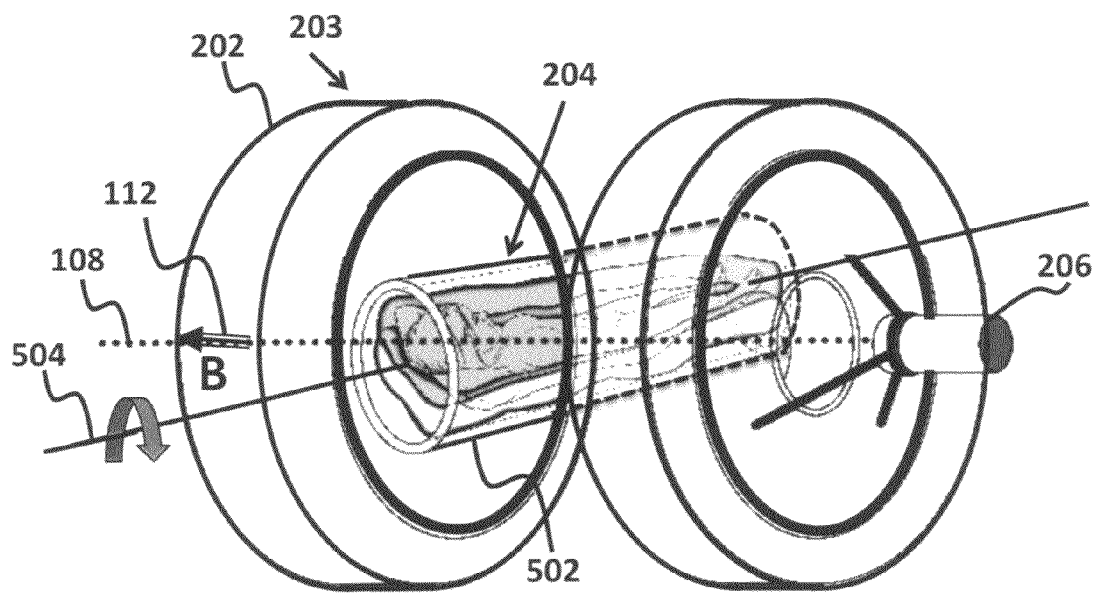

According to another aspect of the invention, FIGS. 5(a)-5(b) show a stationary treatment beam source along the magnetic field with a patient rotating about an axis of a supine position 500. Shown in FIG. 5(a) is a patient 204 disposed in a patient-forming device 502, which can safely envelope the patient 204 and securely rotate the patient 204 about an axis 504 along the head 506 to toe 508 of the patient 204. FIG. 5(b) shows an exemplary integrated MRI-Linac assembly 200, similar to the assembly described in FIG. 2(a), where shown is the patient 204 disposed in the patient-forming device 502 to securely rotate the patient 204 about the axis 504 along the head 506 to toe 508 of the patient 204. It is within the scope of the invention to use other radiotherapy treatment sources as described above in this exemplary embodiment.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. All such variations are considered to be within the scope and spirit of the present invention as defined by the following claims and their legal equivalents.

What is claimed:

1. A radiotherapy treatment apparatus comprising:
   a. a radiotherapy treatment beam;
   b. a magnetic field, wherein said magnetic field is disposed at least parallel to said radiotherapy treatment beam; and
   c. a target, wherein said target is disposed on a supine or prone positioner across said radiotherapy treatment beam, wherein said radiotherapy treatment beam and said magnetic field are disposed to rotate with respect to said target, wherein a source for said magnetic field and a source for said treatment beam are mounted to a rotating ring gantry, wherein said magnetic field source and said treatment beam source rotate about said target.

2. The radiotherapy treatment apparatus of claim 1, wherein said radiotherapy treatment beam comprises a charged particle beam.

3. The radiotherapy treatment apparatus of claim 1, wherein said radiotherapy treatment beam comprises a proton beam.

4. The radiotherapy treatment apparatus of claim 1, wherein said radiotherapy treatment beam comprises an electron beam.

5. The radiotherapy treatment apparatus of claim 1, wherein said radiotherapy treatment beam comprises a linear accelerator (Linac) beam.

6. The radiotherapy treatment apparatus of claim 1, wherein said magnetic field is disposed collinear with said radiotherapy treatment beam.

7. The radiotherapy treatment apparatus of claim 1, wherein said magnetic field is from a magnetic resonance imager (MRI), wherein said MRI is disposed to operate in coordination with operation of said radiotherapy treatment beam.

8. The radiotherapy treatment apparatus of claim 1, wherein said magnetic field is disposed to narrow said radiotherapy treatment beam.

9. The radiotherapy treatment apparatus of claim 1, wherein said rotation comprises rotation up to 360°.

10. The radiotherapy treatment apparatus of claim 1, wherein said target comprises a tumor.

11. The radiotherapy treatment apparatus of claim 1 further comprises a rotation angle dependent shim, wherein said rotation angle dependent shim is disposed to account for Earth's magnetic field.

12. The radiotherapy treatment apparatus of claim 1 further comprises an x-ray imager, wherein said x-ray imager is selected from the group consisting of a megavolt treatment beam x-ray imager, and a kilovolt x-ray imager.

* * * * *